United States Patent [19]
Nelson et al.

[11] Patent Number: 5,877,862
[45] Date of Patent: Mar. 2, 1999

[54] LASER SYSTEM FOR CROSS-ROAD MEASUREMENT OF MOTOR VEHICLE EXHAUST GASES

[75] Inventors: David D. Nelson, N. Chelmsford; J. Barry McManus, Arlington; Mark Zahniser, Lexington; Charles E. Kolb, Sudbury, all of Mass.

[73] Assignee: Aerodyne Research, Inc., Billerica, Mass.

[21] Appl. No.: 918,472

[22] Filed: Aug. 26, 1997

[51] Int. Cl.$^6$ .................................................. G01N 21/00
[52] U.S. Cl. .......................... 356/436; 356/440; 250/343
[58] Field of Search .................................... 356/436–440, 356/320, 326; 250/338.5, 339.13, 343, 345

[56] References Cited

U.S. PATENT DOCUMENTS

| | | | |
|---|---|---|---|
| 4,426,640 | 1/1984 | Becconsall et al. | 356/437 |
| 4,516,858 | 5/1985 | Gelbwachs | 356/437 |
| 5,319,199 | 6/1994 | Stedman et al. | 356/438 |
| 5,498,872 | 3/1996 | Stedman et al. | 356/438 |

*Primary Examiner*—Robert Kim
*Attorney, Agent, or Firm*—Cesari and McKenna, LLP

[57] ABSTRACT

A cross-road motor vehicle exhaust gas analyzer uses tunable infrared laser differential absorption spectroscopy incorporating photon infrared detection to determine the absolute fractional absorption of a laser by the gaseous medium. Spectroscopic constants of the gaseous species of interest are applied to the absolute fractional absorption to calculate the pertinent absolute column densities. In addition to a laser that sweeps across one or more absorption line of an component of interest, the system of the invention includes a laser source tunable over an absorption line of a reference species; the calculated column density of the reference species is used to normalize the concentration of the component of interest to the fuel consumption rate of the motor vehicle.

63 Claims, 2 Drawing Sheets

LASER SYSTEM FOR CROSS-ROAD MEASUREMENT OF MOTOR VEHICLE EXHAUST GASES

FIELD OF THE INVENTION

This invention relates to a system for analyzing the exhaust gases of moving vehicles to ascertain the amounts of various constituents thereof. The system uses a pair of tunable infrared lasers to measure the emissions of atmospheric pollutants, such as NO and CO, by comparing their concentrations with the concentration of $CO_2$ in the exhaust plumes of the vehicles.

BACKGROUND OF THE INVENTION

Improved measurements of pollution emissions by automobiles have become increasingly important as the overall emissions have decreased, since more precision is required to accurately gauge the various pollutants. Instrumentation is available for making accurate measurements in fixed locations, such as garages, where the vehicles are stationary. However, such measurements do not represent vehicle emissions under actual operating conditions; also, vehicle emission standards relying on such periodic measurements can be circumvented.

It is therefore desirable to analyze emissions of individual vehicles "on the fly" so to speak, as they pass measurement sites in the course of normal travel over highways or city streets. Several remote sensing cross-road instruments capable of instantaneously measuring pollutants emitted by passing vehicles have been described. These devices work by directing infrared or ultraviolet radiation across the roadway. Passing cars leave exhaust plumes in the radiation paths and the molecules in the exhaust absorb some of the radiation. The amount of radiation absorbed can be correlated with the column density of the molecular absorber. The column density of carbon dioxide is measured and the emission indices of pollutants are determined as ratios with respect to carbon dioxide. This reference molecule allows meaningful pollutant emission measurements to be made without knowledge of the precise location or extent of dilution of the exhaust plume.

Although these devices have been adequate for monitoring the historically high concentrations of carbon monoxide which they were first developed to measure, they suffer from a relatively low signal-to-noise ratio and they therefore do not provide the desired accuracy for measurement of the concentrations of the various other pollutants present at much lower levels. Specifically, the radiation sources are incoherent, relatively broad-band lamps. The filters used to preferentially pass the absorption frequencies of the various constituents to the detectors pass relative broad-bands of frequencies and the detectors thus receive inputs that are affected by a number of factors in addition to the monitored absorptions. In addition, the broad emitting area of incoherent sources limits the distance that light from these sources can propagate without significant spreading. The spreading over distance traveled of light from incoherent sources can be compensated for with larger beam-forming and collection optics, but such optics greatly increases the cost and complexity of these instruments. Also, these devices cannot calculate the absolute column density of a pollutant and so require frequent field calibration using expensive analyzed gas samples in order to operate in a dependable manner.

SUMMARY OF THE INVENTION

The invention uses Tunable Infrared Laser Differential Absorption Spectroscopy ("TILDAS"), a technique in which a monochromatic beam from a tunable infrared laser is passed through a gaseous medium to a detector and the wavelength of the laser is swept over one or more absorption lines of a molecule of interest whose concentration is to be measured in the gaseous medium. The intensity of the laser beam as received by the detector, when the wavelength corresponds to an absorption line, is compared with the received intensity at other, nonabsorbed wavelengths to ascertain the amount of absorption at the frequency of an absorption line.

Since the beam is essentially monochromatic and its wavelength is known throughout the sweep, the effects of various intensity-varying factors at the nonabsorbed wavelength can be greatly minimized. Laser sources have very small effective source areas, and so the collimating and collecting optics can be of modest size. The analyzer of the invention thus has a greatly improved sensitivity and spectral resolution than instruments known in the prior art. The small spread of the incoherent beams with distance traveled also greatly increases the cross-road range, allowing the system to be used to advantage over multi-lane highways.

In a preferred embodiment, the system of the invention uses beams from two to coherent infrared sources projected over the same path through the monitored atmospheric volume. One of the lasers is operated as described above to detect a pollutant such as carbon monoxide (CO), nitric oxide (NO), nitrous oxide ($N_2O$), nitrogen dioxide ($NO_2$), select hydrocarbons or volatile organic compounds ("VOCs")—for example formaldehyde. The second laser is tuned to measure the concentration of a reference molecule, typically carbon dioxide ($CO_2$). The concentration of the reference molecule is used, as described below, to normalize the readings to the fuel consumption rate of the automobile. This permits the measurement of the monitored pollutant to be converted to the mass of the pollutant per unit of distance traveled, which is the standard against which atmospheric contamination is measured.

Preferably, the system operates to turn each radiation source off after its sweep of its respective frequency range. In conjunction with the use of a highly linear infrared detector, this feature enables the system to determine the absolute fractional absorption of a laser by the gaseous medium. In a preferred embodiment, a processor is configured to apply spectroscopic constants of the pertinent molecules to respective absolute fractional absorption to calculate pertinent absolute column densities. Thus the analyzer of the invention reliably determines concentrations in the gaseous medium without the need for an external calibration reference.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
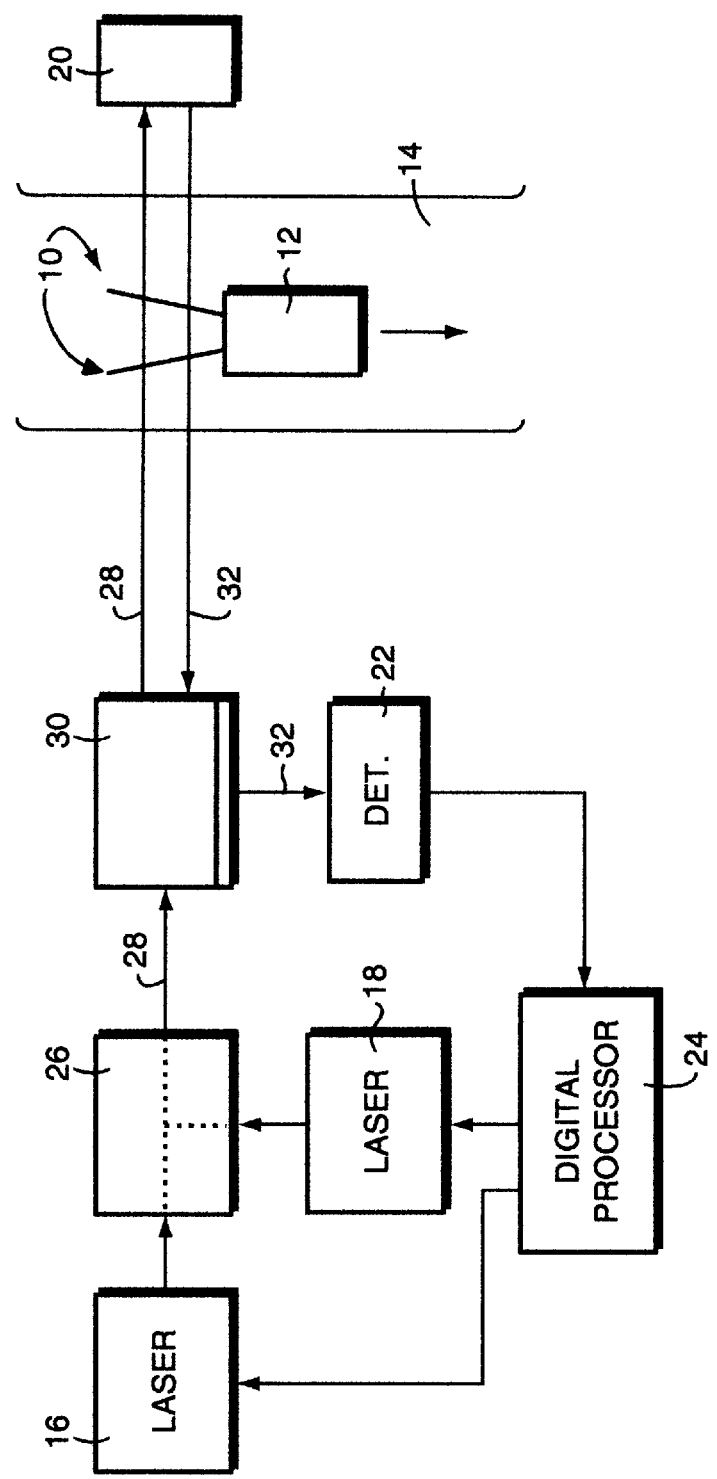
FIG. 1 is a diagram of an analyzer according to the invention.

In FIG. 1 we have depicted an analyzer deployed to measure pollutants in the exhaust gas plumes 10 streaming from automobiles 12 proceeding along a road 14. The analyzer comprises a pair of tunable lasers 16 and 18 whose beams are projected through the plumes 10 to a retroreflector 20 on the opposite side of the road. The reflector 20 returns the beam to a detector 22 which provides a processor 24 with an electric signal indicative of the intensity of the returned beam. The processor 24 is programmed to control the lasers 16 and 18 and provide the analysis functions described herein.

More specifically, the beams from the lasers 16 and 18 are directed to a beam splitter-combiner 26. A beam 28 is projected from the splitter-combiner 26 across the road 14, preferably at approximately tail-pipe height, to the retroreflector 20. The reflector 20 returns a beam 32 along a path parallel to and nearly coincident with the path of the beam 28. A telescope system 30 directs the beam 32 to the infrared radiation detector 22, which senses its intensity. To simplify the drawing, we have omitted therefrom conventional optical component configurations known to those skilled in the art; for example those that are used to collimate beams before they enter the beamsplitter, to aim the beams across the road, or to focus the beams onto the detector.

One of the lasers, e.g. the laser 16, is tunable over a range that includes a wavelength corresponding to an absorption line of $CO_2$. The laser 18 is tunable over a range that includes a wavelength corresponding to an absorption line of a pollutant to be analyzed by the analyzer, e.g. NO, CO or a VOC. The lasers are alternately turned on so that the beam reaching the detector 22 at any given time originated from one or the other of the lasers 16 and 18. Moreover, the processor 24 applies voltage control signals to the lasers so that their respective wavelengths sweep repeatedly through the corresponding absorption lines.

The presence of the plume 10 in the path of the beams 28 and 32 can be detected as follows. Assume that automobiles travel only in the direction of the arrow on the road 14. If one of the lasers, for example the laser 16, is turned on, the passage of the automobile 12 through the beam will interrupt the beam. The processor 24 senses the corresponding output of the detector 22. When the automobile 12 has completed its passage through the beam and the plume 10 is therefore in the beam path, the processor 24 responds to the increased output of the detector 22 by commencing a measurement cycle.

Figure 2:
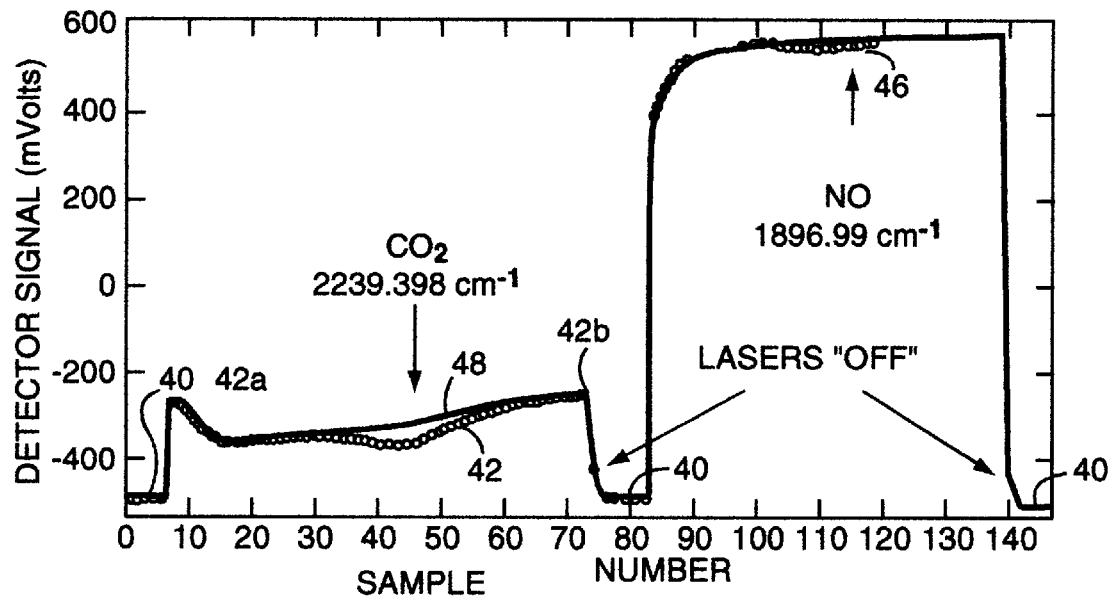
FIG. 2 is a graphical depiction of intensity readings made with the analyzer.

A measurement cycle provides a series of readings that result in the curves 42 and 46 depicted in FIG. 2. Specifically, the processor periodically samples the output of the detector 22, resulting in a curve 42 comprising samples $42_i$ and a curve 46 comprising samples $46_i$. The curves specifically illustrated in the figure correspond to the concentrations of $CO_2$ (curve 42) and NO (curve 46). Initially both lasers are turned off, with a detection response curve 40 corresponding to the background or base level radiation received by the detector 22. The laser 16 is then turned on, with the points $42_i$ in the curve 42 thus corresponding to the intensity of the received laser beam 32 after passage back and forth through the exhaust plume 10 as the laser frequency is swept from a wavelength corresponding to the sample 42a to a wavelength corresponding to the sample 42b. The laser 16 is then turned off and laser 18 turned on, to collect the points $46_i$ making up curve 46.

The foregoing procedure is repeated a number of times, and corresponding samples are then averaged, that is, each indicated sample $42_i$ and $46_i$ in FIG. 2 represents the average value of a number of samples taken at the same laser wavelength in several different sweeps. In this example, we have swept each of the lasers for a duration of 250 $\mu$s, so that approximately 500 $\mu$s is required to generate one complete succession of samples. Each of the sample points in FIG. 2 represents an average acquired from 80 such sweeps, thereby providing a column density for monitored species every 40 ms. The rate at which the measurements can be accomplished depends mainly on the speed of the processor 24, which, in addition to data acquisition and averaging, performs the curve fitting functions described hereinbelow. Typically, time resolutions of 10 milliseconds or better are achievable with systems of the invention.

The curves displayed in FIG. 2 are employed by the processor 24 to calculate absolute column densities of the relevant constituents. The calculation of absolute column densities is based on two important characteristics of the data acquisition system. First, the absolute fractional absorptions of the laser beams are measured; second, these fractional absorptions are interpreted via sophisticated spectral analysis software as absolute column densities. The measurement of absolute fractional absorption is accomplished by turning the lasers off after each frequency sweep and by the use of an infrared photovoltaic detector, whose response voltage is especially linear with respect to the quantity of incident radiation.

Figure 3:
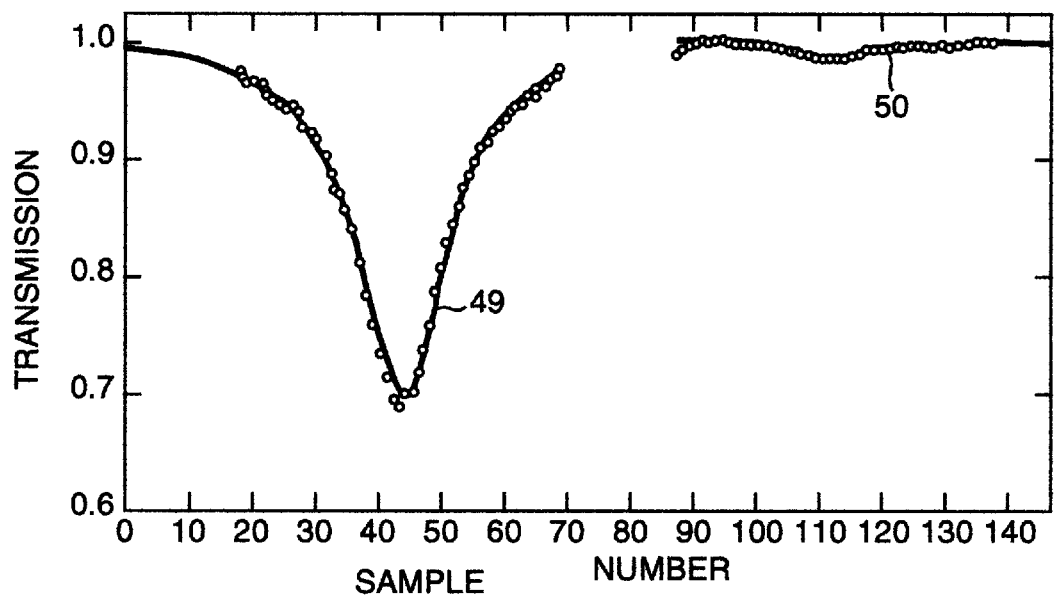
FIG. 3 is a graphical depiction of beam attenuation corresponding to absorption by the pollutants derived from the readings shown in FIG. 2.

In FIG. 2 the curve 48 represents the signal that would be provided by the detector 22 with the laser 16 turned on and in the absence of an absorption line in the frequency range over which the laser swept. If the output of the laser 16 and response of the detector 22 were invariant with laser frequency the curve 48 would be a horizontal straight line. Instead, we use a second- or third-order polynomial to represent this baseline intensity. To obtain the absorptions by $CO_2$ and NO the processor 24 applies a well-known curve-fitting procedure using a Voigt fit to the data represented by the points $42_i$. The points are thus transformed to a succession of sample points 49, (FIG. 3) to which the curve 49 is fitted. By the same process the curve 50 of FIG. 3 is derived from the data points $46_i$ in FIG. 2. The areas under the curves 49 and 50 correlate with the column densities of $CO_2$ and NO respectively. The analyzer's software interprets these absorption curves as column densities using spectroscopic constants which are unchanging properties of the individual molecules being monitored.

The analyzer also takes a series of readings in the absence of an automobile exhaust plume in the path of the laser beams 28 and 32. These readings provide a measure of the background levels of $CO_2$ and NO. The $CO_2$ and NO absorption measurements in the presence of an exhaust plume are then divided, point-by-point, by the measurements made in the absence of a plume to provide normalized $CO_2$ and NO measurements. In an alternative but analogous approach, the analysis described in the previous paragraph may be applied to these normalized data, thereby achieving superior suppression of background interference.

Finally, the typical fuel consumption rate, and thus the $CO_2$ generation rate, of each type automobile is known from previously compiled data, and the $CO_2$ absorption measurement as indicated in FIG. 3 can thus be related to the normalized emission of $CO_2$ and the ratio of the NO absorption to the $CO_2$ absorption thus provides a measure of the NO emission by the automobile.

It will be apparent that the system specifically described herein may be varied in numerous ways without parting from the spirit and scope of the invention. For example, the source of the laser beams provided by the lasers 16 and 18 in the illustrative embodiment may instead reside in a single laser alternately tunable to both of the frequency ranges covered by the distinct lasers 16 and 18. Also, the system of the invention may incorporate the capability to collect data at more than one absorption line of components of interest that would benefit from data collection at more than one of their lines. In another embodiment, the invention may also make measurements of one or more additional pollutants by, for each additional pollutant, incorporating a source of coherent radiation operable over a range including a frequency corresponding to an absorption line of the additional pollutant. The measurement cycle described above then include the additional lasers as well as the lasers 16 and 18 of FIG. 1. This additional coherent radiation source may reside in an additional laser or in a laser also providing the frequency range required for measurement of a first pollutant of interest or of the reference species.

In an alternate embodiment, beams of different frequencies travel simultaneously over paths that are substantially the same as one another. For the purposes of this document, the phrase "substantially the same path" indicates paths that are separated by no more than one centimeter, a distance insignificant compared to the dimension of the exhaust plume along the laser path. Multiple detectors may be used in order to sense the various absorption lines rather than the single detector used in the multiplexed arrangement shown in the illustrative embodiment.

The use of reference species other than carbon dioxide are compatible with the present invention. Water vapor, another product of combustion, is a candidate. Or, automotive fuel could be doped at a known level with a substance unaffected by combustion to provide a reference material.

Also, for roadways for which vehicles pass in two directions optical detectors may be added which, by time differences, ascertain the direction of travel of each of the vehicles. In traffic congestion situations with a significant number of vehicles passing during a given interval, the measurement cycles may be initiated by a clocking arrangement rather than by the passage of individual vehicles as described above. Moreover, the laser beams will be projected at a level and in a direction chosen such that the beams will not be obscured by the passage of the presence of vehicles.

In addition to monitoring emissions from single vehicles, the system of the invention may be used to analyze emissions from groups of vehicles in traffic, for example, in order to ascertain the necessity of relieving congested traffic patterns to avoid harmful pollutant levels or to ascertain whether the standards applied to individual vehicles are sufficient to avoid harmful pollution levels in traffic.

What is claimed is:

1. A system for monitoring a component in the exhaust gas of a moving vehicle, said system comprising:

A. a first laser, tunable over a first frequency range encompassing an absorption line of $CO_2$;

B. a second laser, tunable over a second frequency range encompassing an absorption line of the monitored component;

C. means for sweeping the frequencies of the first and second lasers over said first and second ranges, respectively;

D. means for projecting a first beam from the first laser sweeping over the first range and a second beam from the second laser sweeping over the second range along substantially the same path through said exhaust gas;

E. means for detecting the intensities of said beams after passage through the exhaust gas;

F. means for processing the detected intensities to provide a measure of the concentrations of $CO_2$ and of said component along the path, the means for processing being configured to sample the detected intensities over time so as to generate respective absorption curves of $CO_2$ and of the monitored component; and G. means for comparing the concentrations of the component and of $CO_2$ to determine the rate of emission of the component by the vehicle.

2. The system defined in claim 1 wherein the means for detecting the intensities is a single detector for detecting the intensities of beams from both of said lasers, the means for projecting beams being configured to alternately project the beams from the first and second lasers through said exhaust gas.

3. The system defined in claim 2, further including a retroreflector, the means for projecting beams along substantially the same path including a beamsplitter, the retroreflector and means for projecting beams being configured so that beams from said lasers are overlapped at the beamsplitter and projected through said exhaust gas to the retroreflector and returned by the retroreflector through said exhaust gas along a return route parallel to and nearly coincident with the path.

4. The system defined in claim 3 further including a telescope configured to direct the beam returned by the retroreflector into the means for detecting.

5. The system defined in claim 1 further including a retroreflector, the retroreflector and the means for projecting beams along substantially the same path being configured so that the beams from the lasers are projected through said exhaust gas to the retroreflector and returned by the retroreflector through said exhaust gas.

6. The system defined in claim 1 further including the following:

A. means for measuring the background of concentrations of $CO_2$ and of said component along the path in the absence of a said exhaust gas;

B. means for determining the ratios of the concentrations of each of $CO_2$ and said component in said exhaust gas to the respective background concentrations, thereby to provide normalized concentrations of $CO_2$ and of said component; and C. means for comparing the normalized concentrations of $CO_2$ and said component to ascertain the rate of emission of said component by said vehicle.

7. The system defined in claim 1 wherein the means for detecting the intensities comprises a photovoltaic detector.

8. The system defined in claim 1 wherein the means for sweeping the frequencies of the first and second lasers turns off the first and second lasers after each respective frequency sweep.

9. The system defined in claim 1 wherein the means for processing the detected intensities uses spectroscopic constants in providing a measure of the concentrations of $CO_2$ and of said component along the path.

10. A system for monitoring one or more components of interest in the exhaust gas of a moving vehicle, said system comprising:

A. a source of coherent radiation, tunable over a first range encompassing a first frequency corresponding to an absorption line of a reference species, and tunable over a second range encompassing a second frequency corresponding to an absorption line of a component of interest;

B. means for causing the radiation from each of the ranges to sweep over its respective range;

C. means for projecting a first beam of radiation sweeping over the first range and a second beam of radiation sweeping over the second range over substantially the same path through said exhaust gas;

D. means for detecting the intensities of the first and second beams after projection through the exhaust gas;

E. means for processing the detected intensities to generate respective measures of the concentrations of the reference species and of the component of interest, the means for processing being configured to sample the detected intensities over time so as to generate respective absorption curves of the reference species and of the monitored component; and F. means for comparing the concentrations of the reference species and of the component of interest to determine the rate of emission of the component of interest by the vehicle.

11. The system defined in claim 10 wherein the source of coherent radiation tunable over the first and second ranges comprises one laser, alternately tunable to the first and second frequencies.

12. The system defined in claim 10 wherein the source of coherent radiation tunable over the first and second ranges comprises a first laser tunable to the first range and a second, distinct laser tunable to the second range.

13. The system defined in claim 10 wherein the source of coherent radiation is tunable over a third frequency range encompassing an absorption line of a second component of interest, for monitoring the second component of interest.

14. The system defined in claim 13 wherein the source of coherent radiation is tunable over at least one additional frequency range, the at least one additional frequency range encompassing an absorption line of an additional component of interest, for monitoring the additional component of interest.

15. The system defined in claim 10 wherein the reference species is water vapor.

16. The system defined in claim 10 wherein the reference species is carbon dioxide.

17. The system defined in claim 10 wherein the component of interest is carbon monoxide.

18. The system defined in claim 10 wherein the component of interest is nitric oxide.

19. The system defined in claim 10 wherein the component of interest is a volatile organic compound.

20. The system defined in claim 10 wherein the component of interest is formaldehyde.

21. The system defined in claim 10 wherein the means for causing the radiation from each of the ranges to sweep over its respective range causes each beam to sweep over its respective range for a duration on the order of 250 $\mu$s.

22. The system defined in claim 10 wherein the means for detecting is a single detector, the means for projecting first and second beams being configured to alternately project the first and second beams.

23. The system defined in claim 22 wherein the means for projecting beams along substantially the same path includes a beamsplitter.

24. The system defined in claim 10 further including a retroreflector, the retroreflector and the means for projecting beams along substantially the same path being configured so that the beams from the lasers are projected through said exhaust gas to the retroreflector and returned by the retroreflector through said exhaust gas.

25. The system defined in claim 24 further comprising means for directing light returned by the retroreflector into the detecting means.

26. The system defined in claim 25 wherein the means for directing light comprises a telescope apparatus.

27. The system defined in claim 10 wherein the means for projecting beams along substantially the same path includes a beamsplitter.

28. The system defined in claim 27 further comprising a retroreflector for returning the beam after passage through the exhaust gas along a return route parallel to and nearly coincident with the path.

29. The system defined in claim 28 further comprising means for directing light returned by the retroreflector into the detecting means.

30. The system defined in claim 13 wherein the source of coherent radiation comprises a laser alternately tunable over the third frequency range and over at least one of the first range and the second range.

31. The system defined in claim 1 wherein the means for sweeping the frequencies of the first and second lasers over said first and second ranges causes each of the first beam and the second beam to sweep over its respective range for a duration on the order of 250 $\mu$s.

32. The system defined in claim 1 wherein the means for processing the detected intensities calculates the absolute column densities of the reference species and of the component of interest.

33. The system defined in claim 10 wherein the means for detecting the intensities comprises a photovoltaic detector.

34. The system defined in claim 10 further comprising means for turning off each of the first and second beams after its respective frequency sweep.

35. The system defined in claim 10 wherein the means for processing the detected intensities uses spectroscopic constants in providing a measure of the concentrations of reference species and of the component of interest.

36. The system defined in claim 10 wherein the means for processing the detected intensities calculates the absolute column densities of the reference species and of the component of interest.

37. The system defined in claim 10 wherein the component of interest is nitrous oxide.

38. A method of monitoring one or more components in the exhaust gas of a moving vehicle, the method comprising the steps of:

A. providing a first beam of coherent radiation having a frequency which sweeps over a first frequency range encompassing an absorption line of a reference species;

B. providing a second beam of coherent radiation having a frequency which sweeps over a second frequency range encompassing an absorption line of a component of interest;

C. causing the first and second beams to pass through the exhaust gas over substantially the same path while they are sweeping;

D. detecting and processing the intensities of the first and second beams, after they have passed through the exhaust gas, by sampling the detected intensities over time so as to generate respective absorption curves of the reference species and of the monitored component, to generate respective measures of the concentrations of the reference species and of the component of interest; and E. comparing the concentrations of the reference species and of the component of interest to determine the rate of emission of the component by the vehicle.

39. The method of claim 38 wherein the first and second beams of coherent radiation are produced by a single laser, alternately tunable to the first and second frequencies.

40. The method of claim 38 the first and second beams of coherent radiation are produced by two distinct lasers.

41. The method defined in claim 38 further comprising the step of providing a third beam of coherent radiation having a frequency which sweeps over a third frequency range encompassing an absorption line of a second component of interest, for monitoring the second component of interest.

42. The method defined in claim 41 further comprising the step of providing an additional beam of coherent radiation having a frequency which sweeps over an additional frequency range encompassing an absorption line of an additional component of interest, for monitoring the additional component of interest.

43. The method defined in claim 33 wherein the reference species is water vapor.

44. The method defined in claim 38 wherein the reference species is carbon dioxide.

45. The method defined in claim 38 wherein the component of interest is carbon monoxide.

46. The method defined in claim 38 wherein the component of interest is nitric oxide.

47. The method defined in claim 38 wherein the component of interest is a volatile organic compound.

48. The method defined in claim 38 wherein the component of interest is formaldehyde.

49. The method defined in claim 41 wherein the first, second and third beams of coherent radiation are produced by a single laser, alternately tunable to the first, second and third frequencies.

50. The method defined in claim 38 wherein the step of detecting the intensity of the beams is performed a single detector, the step of causing the first and second beams to pass through the exhaust gas comprising alternately projecting the first and second beams through said exhaust gas.

51. The method defined in claim 38 further comprising the step of reflecting the beams after they have passed through the exhaust gas so that they are returned through said exhaust gas.

52. The method defined in claim 41 wherein the third beam is produced by a laser, the laser also producing at least one of the first and second beams.

53. The method defined in claim 41 wherein the third beam is produced by a laser, neither of the first and second beams being produced by the laser.

54. The method defined in claim 42 wherein the additional beam is produced by a laser, the laser also producing the third beam.

55. The method defined in claim 38 wherein the component of interest is nitrogen dioxide.

56. The method defined in claim 38 wherein the first and second beams of coherent radiation sweep over their respective frequency ranges for a duration on the order of 250 $\mu$s.

57. The method defined in claim 38 wherein the step of detecting the intensities of the first and second beams is performed by a photovoltaic detector.

58. The method defined in claim 38 further comprising the steps of:
   A. turning off each of the first and second beams after its respective frequency sweep; and
   B. measuring radiation while the first and second beams are turned off.

59. The method defined in claim 38 wherein the step of processing the intensities of the first and second beams includes using spectroscopic constants in generating respective measures of the concentrations of the reference species and of the component of interest.

60. The method defined in claim 38 wherein the step of processing the intensities of the first and second beams includes calculating the absolute column densities of the reference species and of the component of interest.

61. The method defined in claim 38 wherein the component of interest is nitrous oxide.

62. The method of claim 38 wherein the step of causing the first and second beams to pass through the exhaust gas over substantially the same path comprises alternately projecting the first and second beams through said exhaust gas, the step of detecting the intensities of the first and second beams being done by a single detector.

63. The method of claim 38 further comprising the steps of:
   A. measuring the background of concentrations of $CO_2$ and of said component along the path in the absence of a said exhaust gas;
   B. determining the ratios of the concentrations of each of $CO_2$ and said component in said exhaust gas to the respective background concentration, thereby to provide normalized concentrations of $CO_2$ and of said component; and
   C. comparing the normalized concentrations of $CO_2$ and said component to ascertain the rate of emission of said component by said vehicle.

* * * * *